United States Patent
Miller et al.

(10) Patent No.: US 7,423,188 B2
(45) Date of Patent: Sep. 9, 2008

(54) AZEOTROPE COMPOSITIONS COMPRISING E-1,3,3,3-TETRAFLUOROPROPENE AND HYDROGEN FLUORIDE AND USES THEREOF

(75) Inventors: Ralph Newton Miller, Newark, DE (US); Mario Joseph Nappa, Newark, DE (US); Velliyur Nott Mallikarjuna Rao, Wilmington, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/590,343

(22) Filed: Oct. 30, 2006

(65) Prior Publication Data

US 2007/0100173 A1    May 3, 2007

Related U.S. Application Data

(60) Provisional application No. 60/732,397, filed on Nov. 1, 2005.

(51) Int. Cl.
*C07C 17/00* (2006.01)
*C07C 17/38* (2006.01)

(52) U.S. Cl. ...................... 570/155; 570/178
(58) Field of Classification Search .............. 570/155, 570/178
See application file for complete search history.

(56) References Cited

U.S. PATENT DOCUMENTS

| 5,918,481 | A | * | 7/1999 | Pham et al. | 62/631 |
| 5,986,151 | A | * | 11/1999 | Van Der Puy | 570/175 |
| 6,472,573 | B1 | * | 10/2002 | Yamamoto et al. | 570/164 |
| 2005/0090698 | A1 | | 4/2005 | Merkel et al. | |

FOREIGN PATENT DOCUMENTS

| EP | 0 974 571 A2 | 1/2000 |
| EP | 1 067 106 A1 | 1/2001 |

OTHER PUBLICATIONS

Szapiro, variation of azeotropic composition with pressure, Zesyty Nauk. Politech. Lodz. Chem. (1958), No. 7, 3-16.*
PCT International Search Report dated May 16, 2007 for International Application No. PCT/US2006/042668.

* cited by examiner

*Primary Examiner*—Jafar Parsa

(57) ABSTRACT

Disclosed herein are azeotrope and near-azeotrope compositions comprising E-1,3,3,3-tetrafluoropropene and hydrogen fluoride. These azeotrope and near-azeotrope compositions are useful in processes to produce E-1,3,3,3-tetrafluoropropene and in processes to purify E-1,3,3,3-tetrafluoropropene from mixtures of E-1,3,3,3-tetrafluoropropene with 1,1,1,3,3-pentafluoropropane and/or with hydrogen fluoride.

22 Claims, 1 Drawing Sheet

US 7,423,188 B2

AZEOTROPE COMPOSITIONS COMPRISING E-1,3,3,3-TETRAFLUOROPROPENE AND HYDROGEN FLUORIDE AND USES THEREOF

CROSS REFERENCE TO RELATED APPLICATIONS

This application claims priority to U.S. application Ser. No. 60/732,397, the complete disclosure of which is incorporated herein by reference.

BACKGROUND OF THE INVENTION

1. Field of the Invention

Disclosed herein are azeotrope compositions comprising E-1,3,3,3-tetrafluoropropene and hydrogen fluoride. The azeotrope compositions are useful in processes to produce and in processes to purify E-1,3,3,3-tetrafluoropropene.

2. Description of Related Art

Chlorine-containing compounds, such as chlorofluorocarbons (CFCs) are considered to be detrimental to the Earth's ozone layer. Many of the hydrofluorocarbons (HFCs), used to replace CFCs, have been found to contribute to global warming. Therefore, there is a need to identify new compounds that do not damage the environment, but also possess the properties necessary to function as refrigerants, solvents, cleaning agents, foam blowing agents, aerosol propellants, heat transfer media, dielectrics, fire extinguishing agents, sterilants and power cycle working fluids. Fluorinated olefins, containing one or more hydrogens in the molecule, are being considered for use in some of the applications, like for example in refrigeration.

BRIEF SUMMARY OF THE INVENTION

One aspect relates to an azeotrope or near-azeotrope composition comprising E-1,3,3,3-tetrafluoropropene (E-HFC-1234ze) and hydrogen fluoride.

A further aspect relates to a process for the separation of E-HFC-1234ze from 1,1,1,3,3,-pentafluoropropane (HFC-245fa) comprising:
a) forming a mixture of E-HFC-1234ze, HFC-245fa, and hydrogen fluoride; and b) subjecting said mixture to a distillation step forming a column distillate composition comprising an azeotrope or near-azeotrope composition of hydrogen fluoride and E-HFC-1234ze essentially free of HFC-245fa.

A further aspect relates to a process for the separation of E-HFC-1234ze from a mixture comprising an azeotrope or near-azeotrope composition of E-HFC-1234ze and hydrogen fluoride, said process comprising: a) subjecting said mixture to a first distillation step in which a composition enriched in either (i) hydrogen fluoride or (ii) E-HFC-1234ze is removed as a first distillate composition with a first bottoms composition being enriched in the other of said components (i) or (ii); and b) subjecting said first distillate composition to a second distillation step conducted at a different pressure than the first distillation step in which the component enriched as first bottoms composition in (a) is removed in a second distillate composition with a second bottoms composition enriched in the same component which was enriched in the first distillate composition.

A further aspect relates to a process for the purification of E-HFC-1234ze from a mixture of E-HFC-1234ze, HFC-245fa, and hydrogen fluoride, said process comprising: a) subjecting said mixture to a first distillation step to form a first distillate comprising an azeotrope or near-azeotrope composition containing E-HFC-1234ze and hydrogen fluoride and a first bottoms comprising HFC-43-10mee;
b) subjecting said first distillate to a second distillation step from which a composition enriched in either (i) hydrogen fluoride or (ii) E-HFC-1234ze is removed as a second distillate composition with a second bottoms composition being enriched in the other of said components (i) or (ii); and
c) subjecting said second distillate composition to a third distillation step conducted at a different pressure than the second distillation step in which the component enriched in the second bottoms composition in (b) is removed in a third distillate composition with a third bottoms composition enriched in the same component that was enriched in the second distillate composition.

A further aspect relates to a process to produce E-HFC-1234ze comprising: a) feeding HFC-245fa to a reaction zone for dehydrofluorination to form a reaction product composition comprising E-HFC-1234ze, unreacted HFC-245fa and hydrogen fluoride; b) subjecting said reaction product composition to a first distillation step to form a first distillate composition comprising an azeotrope or near-azeotrope composition containing E-HFC-1234ze and hydrogen fluoride and a first bottoms composition comprising HFC-245fa; c) subjecting said first distillate composition to a second distillation step from which a composition enriched in either (i) hydrogen fluoride or (ii) E-HFC-1234ze is removed as a second distillate composition with a second bottoms composition being enriched in the other of said components (i) or (ii); and
d) subjecting said second distillate composition to a third distillation step conducted at a different pressure than the second distillation step in which the component enriched in the second bottoms composition in (c) is removed in a third distillate composition with a third bottoms composition enriched in the same component that was enriched in the second distillate composition.

BRIEF DESCRIPTION OF THE DRAWING(S)

DETAILED DESCRIPTION OF THE INVENTION

Figure 2:
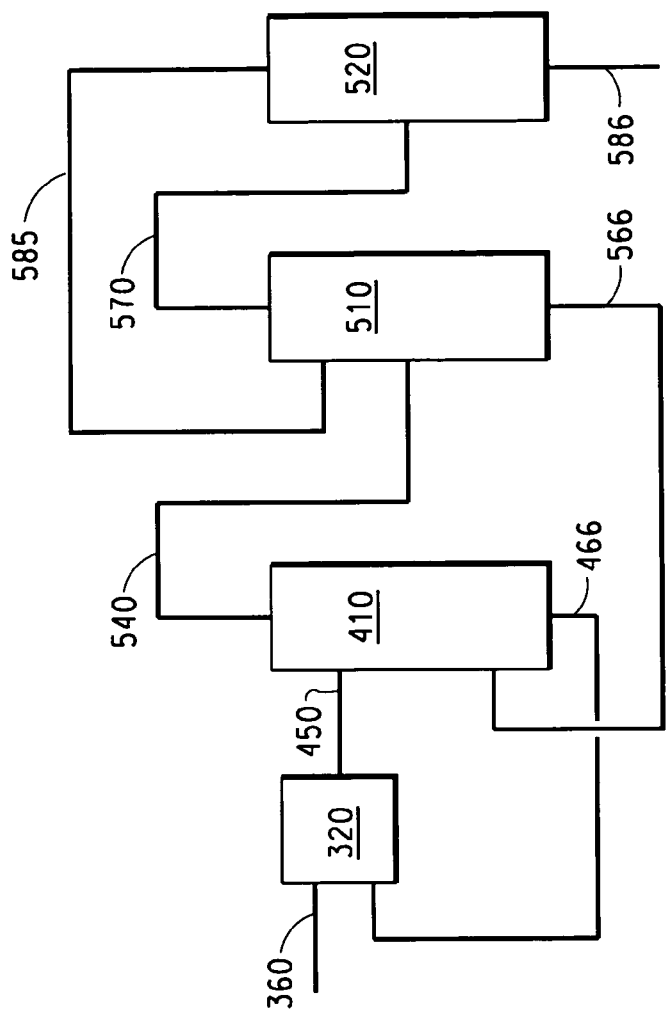
FIG. 2 is a schematic flow diagram illustrating one embodiment for practicing a process for production of E-HFC-1234ze.

One aspect relates to compositions containing 1,3,3,3-tetrafluoropropene (E-HFC-1234ze, $CF_3CH=CHF$). HFC-1234ze may exist as one of two configurational isomers, E or Z. E-HFC-1234ze as used herein refers to a mixture of the isomers, E-HFC-1234ze (CAS reg no. 29118-24-9) or Z-HFC-1234ze (CAS reg. no. 29118-25-0), wherein the predominant isomer is E-HFC-1234ze. E-HFC-1234ze may be prepared by methods known in the art, such as those described in U.S. Pat. Nos. 5,895,825, 5,986,151, 6,031,141, and 6,548,719, and also by methods disclosed in WO 2004/018093, WO 2004/018095, and JP 1999/140002, all of which are incorporated herein by reference.

As used herein, predominant isomer is intended to mean that isomer which is present in the composition at a concentration of greater than 50 mole percent, preferably greater than 60 mole percent, more preferably greater than 70 mole percent, even more preferably greater than 80 mole percent, and most preferably greater than 90 mole percent.

Anhydrous hydrogen fluoride (HF) has CAS reg. no. 7664-39-3 and is commercially available.

Also useful in the processes disclosed herein is 1,1,1,3,3-pentafluoropropane (HFC-245fa, $CF_3CH_2CHF_2$, CAS reg. no. 431-63-0). HFC-245fa may be prepared by methods known in the art.

In considering a process for the dehydrofluorination of HFC-245fa to E-HFC-1234ze and HF and the isolation of E-HFC-1234ze from such a process, it has been discovered surprisingly that the hydrofluoroolefin E-HFC-1234ze forms an azeotrope with HF.

One aspect provides a composition, which comprises E-HFC-1234ze and an effective amount of hydrogen fluoride (HF) to form an azeotrope composition. By effective amount is meant an amount, which, when combined with E-HFC-1234ze, results in the formation of an azeotrope or near-azeotrope mixture. As recognized in the art, an azeotrope or a near-azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

For the purpose of this discussion, near-azeotrope composition (also commonly referred to as an "azeotrope-like composition") means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-azeotrope compositions in which during boiling or evaporation, the liquid composition changes to a substantial degree.

Additionally, near-azeotrope compositions exhibit dew point pressure and bubble point pressure with virtually no pressure differential. That is to say that the difference in the dew point pressure and bubble point pressure at a given temperature will be a small value. It may be stated that compositions with a difference in dew point pressure and bubble point pressure of less than or equal to 3 percent (based upon the bubble point pressure) may be considered to be a near-azeotrope.

Accordingly, the essential features of an azeotrope or a near-azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope or near-azeotrope liquid composition is subjected to boiling at different pressures. Thus, an azeotrope or a near-azeotrope composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotrope compositions (including their boiling points at particular pressures) may be calculated (see, e.g., W. Schotte Ind. Eng. Chem. Process Des. Dev. (1980) 19, 432-439). Experimental identification of azeotrope compositions involving the same components may be used to confirm the accuracy of such calculations and/or to modify the calculations at the same or other temperatures and pressures.

Compositions may be formed that comprise azeotrope combinations of hydrogen fluoride with E-HFC-1234ze. These include compositions comprising from about 27.3 mole percent to about 31.6 mole percent HF and from about 72.7 mole percent to about 68.4 mole percent E-HFC-1234ze (which forms an azeotrope boiling at a temperature from between about −20° C. and about 100° C. and at a pressure from between about 15.5 psi (107 kPa) and about 539 psi (3716 kPa)).

Additionally, near-azeotrope compositions containing HF and E-HFC-1234ze may also be formed. Such near-azeotrope compositions comprise about 62.4 mole percent to about 89.4 mole percent E-HFC-1234ze and about 37.6 mole percent to about 10.6 mole percent HF at temperatures ranging from about −20° C. to about 100° C. and at pressures from about 2.8 psi (19 kPa) to about 518 psi (3571 kPa).

Compositions may be formed that consist essentially of azeotrope combinations of hydrogen fluoride with E-HFC-1234ze. These include compositions consisting essentially of from about 27.3 mole percent to about 31.6 mole percent HF and from about 72.7 mole percent to about 68.4 mole percent E-HFC-1234ze (which forms an azeotrope boiling at a temperature from between about −20° C. and about 100° C. and at a pressure from between about 15.5 psi (107 kPa) and about 539 psi (3716 kPa)).

Near azeotrope compositions may also be formed that consist essentially of about 62.4 mole percent to about 89.4 mole percent E-HFC-1234ze and about 37.6 mole percent to about 10.6 mole percent HF at temperatures ranging from about −20° C. to about 100° C. and at pressures from about 2.8 psi (19 kPa) to about 518 psi (3571 kPa).

At atmospheric pressure, the boiling points of hydrofluoric acid and E-HFC-1234ze are about 19.5° C. and −19° C., respectively. The relative volatility at 70 psi (483 kPa) and 20.0° C. of HF and E-HFC-1234ze was found to be nearly 1.0 as 30.7 mole percent HF and 69.3 mole percent E-HFC-1234ze was approached. The relative volatility at 273 psi (1882 kPa) and 70° C. was found to be nearly 1.0 as 31.4 mole percent HF and 68.6 mole percent E-HFC-1234ze was approached. These data indicate that the use of conventional distillation procedures will not result in the separation of a substantially pure compound because of the low value of relative volatility of the compounds.

To determine the relative volatility of HF with E-HFC-1234ze, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126, the entire disclosure of which is hereby incorporated by reference. Samples of the vapor and liquid, or vapor and each of the two liquid phases under those conditions where two liquid phases exist, were obtained and analyzed to verify their respective compositions.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", $4^{th}$ Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HF and E-HFC-1234ze behave in an ideal manner, and can sufficiently predict the relative volatilities of the components in such mixtures. Thus, while HF has a good relative volatility compared to E-HFC-1234ze at low E-HFC-1234ze concentrations, the relative volatility becomes nearly 1.0 as 69.3 mole percent E-HFC-1234ze was approached at 20° C. This would make it impossible to separate E-HFC-1234ze from HF by conventional distillation from such a mixture. Where the relative volatility approaches 1.0 defines the system as forming a near-azeotrope or azeotrope composition.

It has been found that azeotropes of HFC-1234ze and HF are formed at a variety of temperatures and pressures. Azeotrope compositions may be formed between 107 kPa (at a temperature of –20° C.) and 3716 kPa (at a temperature of 100° C.) said compositions consisting essentially of E-HFC-1234ze and HF range from about 27.3 mole percent HF (and 72.7 mole percent E-HFC-1234ze) to about 31.6 mole percent HF (and 68.4 mole percent E-HFC-1234ze). An azeotrope of HF and E-HFC-1234ze has been found at 20° C. and 70 psi (483 kPa) consisting essentially of about 30.7 mole percent HF and about 69.3 mole percent E-HFC-1234ze. An azeotrope of HF and E-HFC-1234ze has also been found at 70° C. and 273 psi (1882 kPa) consisting essentially of about 31.4 mole percent HF and about 68.6 mole percent E-HFC-1234ze. Based upon the above findings, azeotrope compositions at other temperatures and pressures may be calculated. It has been calculated that an azeotrope composition of about 27.3 mole percent HF and about 72.7 mole percent E-HFC-1234ze can be formed at –20° C. and 15.5 psi (107 kPa); an azeotrope composition of about 31.6 mole percent HF and about 68.4 mole percent E-HFC-1234ze can be formed at 60° C. and 215 psi (1482 kPa); and an azeotrope composition of about 29.4 mole percent HF and about 70.6 mole percent E-HFC-1234ze can be formed at 100° C. and 539 psi (3716 kPa). Accordingly, one aspect provides an azeotrope composition consisting essentially of from about 27.3 mole percent to about 31.6 mole percent HF and from about 72.7 mole percent to about 68.4 mole percent E-HFC-1234ze, said composition having a boiling point of about –20° C. to about 100° C. at 15.5 psi (107 kPa) to about 539 psi (3716 kPa).

It has also been found that azeotrope or near-azeotrope compositions may be formed between about 2.9 psi (20 kPa) to about 518 psi (3571 kPa) at temperatures ranging from about -20° C. to about 100° C., said compositions consisting essentially of about 62.4 mole percent to about 89.4 mole percent E-HFC-1234ze and about 37.6 mole percent to about 10.6 mole percent HF.

The HF/E-HFC-1234ze azeotrope and near-azeotrope compositions are useful in processes to produce E-HFC-1234ze and in processes to purify E-HFC-1234ze. In fact, the HF/E-HFC-1234ze azeotrope and near-azeotrope compositions may be useful in any process that creates a composition containing E-HFC-1234ze and HF.

Azeotropic distillation may be carried out to separate E-HFC-1234ze from HFC-245fa, which is the starting material for production of E-HFC-1234ze, by vapor phase dehydrofluorination. A two-column azeotropic distillation may then be carried out to separate the co-produced HF from the desired E-HFC-1234ze product. And another two-column azeotropic distillation may be carried out to separate HF from HFC-245fa. HF may be removed from the halogenated hydrocarbon components of the product mixture using, for example, standard aqueous solution scrubbing techniques. However, the production of substantial amounts of scrubbing discharge can create aqueous waste disposal concerns. Thus, there remains a need for processes utilizing HF from such product mixtures.

While the initial mixture treated in accordance with the processes disclosed herein can be obtained from a variety of sources, including by adding E-HFC-1234ze to HF-containing compositions, an advantageous use of the present processes resides in treating the effluent mixtures from the preparation of E-HFC-1234ze.

E-HFC-1 234ze may be prepared by the vapor phase dehydrofluorination of HFC-245fa as in WO2004/018093 and WO2004/018095, both of which are incorporated herein by reference.

Another aspect provides a process for the separation of E-HFC-1234ze from HFC-245fa comprising: a) forming a mixture of E-HFC-1234ze, HFC-245fa, and hydrogen fluoride; and b) subjecting said mixture to a distillation step forming a column distillate composition comprising an azeotrope or near-azeotrope composition of HF and E-HFC-1234ze essentially free of HFC-245fa.

As described herein, by "essentially free of HFC-245fa" is meant that the composition contains less than about 100 ppm (mole basis), preferably less than about 10 ppm and most preferably less than about 1 ppm, of HFC-245fa.

This azeotropic distillation takes advantage of the low boiling azeotrope composition formed by E-HFC-1234ze and HF. The azeotrope composition boils at a temperature lower than the boiling point of either pure component and lower than the boiling point of HFC-245fa as well.

As stated previously, the mixture of E-HFC-1234ze, HFC-245fa and HF may be formed by any practical means. Generally, the present process is particularly useful for the separation of E-HFC-1 234ze from the reaction mixture produced by the dehydrofluorination of HFC-245fa. HF is a co-product formed in this dehydrofluorination reaction. The reaction mixture produced may then be treated by the instant process to remove HFC-245fa. The E-HFC-1234ze is taken overhead as the distillate from the distillation column as an azeotrope or near-azeotrope composition of E-HFC-1234ze with HF. The HFC-245fa is taken out of the bottom of the column as a bottoms composition and may contain some amount of HF, as well. The amount of HF in the HFC-245fa from the bottom of the distillation column may vary from about 38 mole percent to less than 1 part per million (ppm, mole basis) depending on the manner in which the dehydrofluorination reaction is conducted. In fact, if the dehydrofluorination reaction is conducted in a manner to provide 50 percent conversion of the HFC-245fa and the reaction mixture leaving the reaction zone is fed directly to the distillation step, the HFC-245fa leaving the bottom of the distillation process will contain about 37 mole percent HF.

In one embodiment, operating the present azeotropic distillation involves providing an excess of E-HFC-1234ze to the distillation column. If the proper amount of E-HFC-1234ze is fed to the column, then all the HF may be taken overhead as an azeotrope composition containing E-HFC-1234ze and HF. Thus, the HFC-245fa removed from the column bottoms will be essentially free of HF.

As described herein, by "essentially free of HF" is meant that the composition contains less than about 100 ppm (mole basis), preferably less than about 10 ppm and most preferably less than about 1 ppm, of HF.

In the distillation step, the distillate exiting the distillation column overhead comprising HF and E-HFC-1234ze may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step depend upon a number of parameters, such as the diameter of the distillation column, feed points, and the number of separation stages in the column, among others. The operating pressure of the distillation column may range from about 10 psi pressure to about 200 psi (1380 kPa), normally about 20 psi to about 50 psi. The distillation column is typically operated at a pressure of about 25 psi (172 kPa) with a bottoms temperature of about 30° C. and a tops temperature of about −7° C. Normally, increasing the reflux ratio results in increased distillate stream purity, but generally the reflux ratio ranges between 0.5/1 to 100/1. The temperature of the condenser, which is located adjacent to the top of the column, is normally sufficient to substantially fully condense the distillate that is exiting from the top of the column, or is that temperature required to achieve the desired reflux ratio by partial condensation.

The column distillate composition comprising an azeotrope or near-azeotrope composition of HF and E-HFC-1234ze, essentially free of HFC-245fa, must be treated to remove the HF and provide pure E-HFC-1234ze as product. This may be accomplished, for example, by neutralization or by a second distillation process, as described herein.

A further aspect provides a process for the separation of E-HFC-1234ze from a mixture comprising an azeotrope or near-azeotrope composition of E-HFC-1234ze and HF, said process comprising: a) subjecting said mixture to a first distillation step in which a composition enriched in either (i) hydrogen fluoride or (ii) E-HFC-1234ze is removed as a first distillate composition with a first bottoms composition being enriched in the other of said components (i) or (ii); and b) subjecting said first distillate composition to a second distillation step conducted at a different pressure than the first distillation step in which the component enriched as first bottoms composition in (a) is removed in a second distillate composition with a second bottoms composition enriched in the same component which was enriched in the first distillate composition.

The process as described above takes advantage of the change in azeotrope composition at different pressures to effectuate the separation of E-HFC-1234ze and HF. The first distillation step may be carried out at high pressure relative to the second distillation step. At higher pressures, the HF/E-HFC-1234ze azeotrope contains less E-HFC-1234ze. Thus, this high-pressure distillation step produces an excess of E-HFC-1234ze, which boiling at a higher temperature than the azeotrope will exit the column as the bottoms as pure E-HFC-1234ze. The first column distillate is then fed to a second distillation step operating at lower pressure. At the lower pressure, the HF/E-HFC-1234ze azeotrope shifts to lower concentrations of HF. Therefore, in this second distillation step, there exists an excess of HF. The excess HF, having a boiling point higher than the azeotrope, exits the second distillation column as the bottoms composition.

The endothermic dehydrofluorination reaction of HFC-245fa to produce E-HFC-1234ze may be accomplished, for example, in a tubular reactor with catalyst in the tubes and with a heating medium on the shellside of the reactor. Alternatively, a heat carrier may be used to permit adiabatic operation. Either pure HFC-245fa or pure E-HFC-1234ze, both being produced by the distillation processes described herein, may be recycled back to the reactor to serve as heat carrier. HFC-245fa would be a preferred heat carrier, as introduction of E-HFC-1234ze to the dehydrofluorination reactor will result in a reduction in single-pass conversion of HFC-245fa.

In both the first and second distillation steps, the distillate exiting the distillation column overhead comprising HF and E-HFC-1234ze may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step depend upon a number of parameters, such as the diameter of the distillation column, feed points, and the number of separation stages in the column, among others. The operating pressure of the first distillation column may range from about 50 psi (345 kPa) pressure to about 225 psi (1550 kPa), normally about 50 psi (345 kPa) to about 100 psi (690 kPa). The first distillation column is typically operated at a pressure of about 70 psi (483 kPa) with a bottoms temperature of about 76° C. and a tops temperature of about 69° C. Normally, increasing the reflux ratio results in increased distillate stream purity, but generally the reflux ratio ranges between 0.1/1 to 100/1. The temperature of the condenser, which is located adjacent to the top of the column, is normally sufficient to substantially fully condense the distillate that is exiting from the top of the column, or is that temperature required to achieve the desired reflux ratio by partial condensation.

The operating pressure of the second distillation column may range from about 5 psi (34 kPa) pressure to about 50 psi (345 kPa), normally about 5 psi (34 kPa) to about 20 psi (138 kPa). The second distillation column is typically operated at a pressure of about 17 psi (117 kPa) with a bottoms temperature of about 26° C. and a tops temperature of about −18° C. Normally, increasing the reflux ratio results in increased distillate stream purity, but generally the reflux ratio ranges between 0.1/1 to 50/1. The temperature of the condenser, which is located adjacent to the top of the column, is normally sufficient to substantially fully condense the distillate that is exiting from the top of the column, or is that temperature required to achieve the desired reflux ratio by partial condensation.

Figure 1:
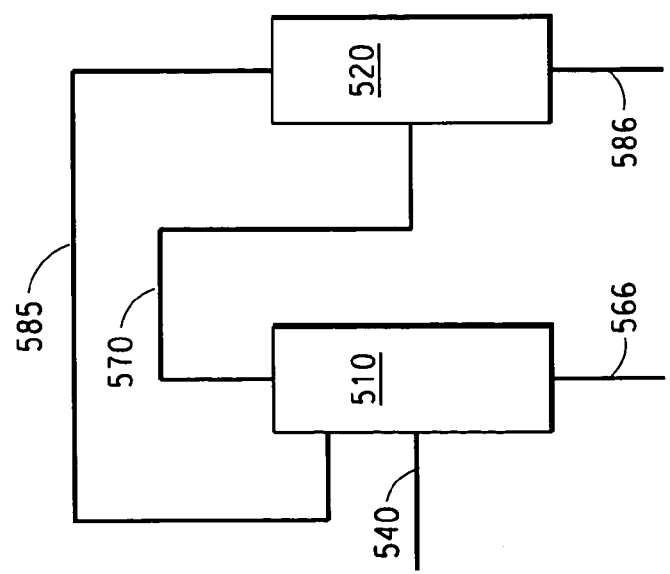
FIG. 1 is a schematic flow diagram illustrating one embodiment for practicing a two-column azeotropic distillation process.

FIG. 1 is illustrative of one embodiment for practicing the present two-column distillation process for the separation of E-HFC-1234ze and HF. Referring to FIG. 1, a feed mixture derived from a prior azeotropic distillation comprising HF and E-HFC-1234ze, wherein the molar ratio of HF:E-HFC-1234ze is about 0.48:1 (or lower), is passed through line (540) to a multiple stage distillation column (510), operating at a temperature of about 69° C. and a pressure of about 265 psi (1827 kPa). The bottoms of the distillation column (510), containing essentially pure E-HFC-1234ze at a temperature of about 76° C. and a pressure of about 267 psi (1841 kPa) is removed from the bottom of column (510) through line (566). The distillate from column (510), containing the HF/E-HFC-1234ze azeotrope (HF:E-HFC-1234ze molar ratio is about 0.45:1) at a temperature of about 69° C. and a pressure of about 265 psi (1827 kPa) is removed from the top of column (510) and sent through line (570) to a multiple stage distillation column (520). The distillate from column (520), containing the HF/E-HFC-1234ze azeotrope (molar ratio is about 0.39:1) at a temperature of about −18° C. and a pressure of about 17 psi (117 kPa), is removed from column (520) through line (585) and is recycled back to column (510). The bottoms of column (520) containing essentially pure HF at a temperature of about 26° C. and a pressure of about 19 psi (131 kPa) is removed through line (586).

U.S. Pat. No. 6,755,942, herein incorporated by reference, discloses azeotrope and near-azeotrope compositions consisting essentially of HFC-245fa and HF ranging from about 16 mole percent to about 56 mole percent HFC-245fa and from about 84 mole percent to about 44 mole percent HF. The existence of this azeotrope allows the separation of HFC-245fa from HF to be accomplished in a similar manner to the separation of E-HFC-1234ze from HF, that being a two-column azeotropic distillation. Such a two column azeotropic distillation is also described in U.S. Pat. No. 6,755,942.

A further aspect provides a process for the purification of E-HFC-1234ze from a mixture of E-HFC-1234ze, HFC-245fa, and HF, said process comprising: a) subjecting said mixture to a first distillation step to form a first distillate comprising an azeotrope or near-azeotrope composition containing E-HFC-1234ze and HF and a first bottoms comprising HFC-43-10mee; b) subjecting said first distillate to a second distillation step from which a composition enriched in either (i) hydrogen fluoride or (ii) E-HFC-1234ze is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed in a third distillate composition with a third bottoms composition enriched in the same component that was enriched in the second distillate composition.

A further aspect provides a process to produce E-HFC-1234ze comprising: a) feeding HFC-245fa to a reaction zone for dehydrofluorination to form a reaction product composition comprising E-HFC-1234ze, unreacted HFC-245fa and hydrogen fluoride; b) subjecting said reaction product composition to a first distillation step to form a first distillate composition comprising an azeotrope or near-azeotrope composition containing E-HFC-1234ze and HF and a first bottoms composition comprising HFC-245fa; c) subjecting said first distillate composition to a second distillation step from which a composition enriched in either (i) hydrogen fluoride or (ii) E-HFC-1234ze is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (c) is removed in a third distillate composition with a third bottoms composition enriched in the same component that was enriched in the second distillate composition. Optionally, the process may further comprise recycling at least some portion of said first bottoms composition to said reaction zone. Optionally, the process may further comprise recycling at least some portion of said second bottoms composition or said third bottoms composition to said reaction zone. Optionally, the process may further comprise recycling at least some portion of said second bottoms composition or said third bottoms composition to said first distillation step. Optionally, the process may further comprise recovering at least some portion of said second bottoms composition or said third bottoms composition as E-HFC-1234ze essentially free of HFC-245fa and HF.

As described herein, by "essentially free of HFC-245fa and HF" is meant that the composition contains less than about 100 ppm (mole basis), preferably less than about 10 ppm and most preferably less than about 1 ppm, of each of HFC-245fa and HF.

The reaction zone for the dehydrofluorination may comprise a flow reactor preferably containing a fixed bed of dehydrofluorination catalyst. The process equipment for all the processes disclosed herein and the associated feed lines, effluent lines and associated units may be constructed of materials resistant to hydrogen fluoride. Typical materials of construction, well-known to the art, include stainless steels, in particular of the austenitic type, and the well-known high nickel alloys such as Monel® nickel-copper alloys, Hastelloy® nickel based alloys and Inconel® nickel-chromium alloys.

FIG. 2 is illustrative of one embodiment for practicing the present process for production of E-HFC-1234ze. HFC-245fa is fed through line (360) to reactor (320). The reactor effluent mixture comprising HF, HFC-245fa and E-HFC-1234ze, exits the reactor through line (450) and is fed to a multiple stage distillation column (410). The bottoms of distillation column (410), containing essentially pure HFC-245fa is removed from the bottom of column (410) through line (466) and may be recycled back to the reactor. The distillate from column (410), containing the HF/E-HFC-1234ze azeotrope is removed from the top of column (410) and is sent through line (540) to a second multiple stage distillation column (510). The bottoms from column (510), which is essentially pure E-HFC-1234ze, is removed from column (510) through line (566) and may be recycled back to the reactor (320) as a heat carrier. The distillate from column (510), containing the HF/E-HFC-1234ze azeotrope, is fed through line (570) to a third multiple stage distillation column (520). The distillate from column (520) comprising HF/E-HFC-1234ze is removed through line (585) and may be recycled to the second distillation column (510). The bottoms composition from column (520) is essentially pure HF and is removed from column (520) through line (586). The essentially pure HF product from this process may be used in any manner appropriate such as feeding to a fluorination reactor for production of a fluorochemical compound, or may be neutralized for disposal.

While not illustrated in the figures, it is understood that certain pieces of process equipment may be used in the processes described herein, for optimization. For instance, pumps, heaters or coolers may be used where appropriate. As an example, it is desirable to have the feed to a distillation column at the same temperature as the point in the column that it is fed. Therefore, heating or cooling of the process stream may be necessary to match the temperature.

Without further elaboration, it is believed that one skilled in the art can, using the description herein, utilize the disclosed compositions and processes to their fullest extent. The following exemplary embodiments are, therefore, to be construed as merely illustrative, and do not constrain the remainder of the disclosure in any way whatsoever.

EXAMPLES

Example 1

Phase Studies of Mixtures of HF and E-HFC-1234ze

A phase study was performed for a composition consisting essentially of E-HFC-1234ze and HF, wherein the composition was varied and the vapor pressures were measured at both 20° C. and 70° C. Based upon the data from the phase studies, azeotropic compositions at other temperature and pressures have been calculated.

Table 1 provides a compilation of experimental and calculated azeotropic compositions for HF and E-HFC-1234ze at specified temperatures and pressures.

TABLE 1

| Temperature, ° C. | Pressure, psi (kPA) | Mole % HF | Mole % E-HFC-1234ze |
|---|---|---|---|
| −20 | 15.5 (107) | 27.3 | 72.7 |
| 0 | 35.6 (242) | 29.7 | 70.3 |
| 20 | 70.4 (485) | 30.7 | 69.3 |
| 40 | 127 (878) | 31.5 | 68.5 |
| 60 | 215 (1482) | 31.6 | 68.4 |
| 65 | 242 (1669) | 31.5 | 68.5 |
| 70 | 273 (1881) | 31.4 | 68.6 |
| 75 | 307 (2117) | 31.2 | 68.8 |
| 80 | 345 (2376) | 31.0 | 69.0 |
| 85 | 386 (2661) | 30.7 | 69.3 |
| 90 | 431 (2972) | 30.4 | 69.6 |
| 95 | 482 (3323) | 30.0 | 70.0 |
| 100 | 539 (3715) | 29.5 | 70.5 |

Example 2

Dew Point and Bubble Point Vapor Pressures

The dew point and bubble point vapor pressures for compositions disclosed herein were calculated from measured and calculated thermodynamic properties. The near-azeotrope range is indicated by the minimum and maximum concentration of E-HFC-1234ze (mole percent, mol %) for which the difference in dew point and bubble point pressures is less than or equal to 3% (based upon bubble point pressure). The results are summarized in Table 2.

TABLE 2

| Temperature, ° C. | Azeotrope composition, mol % E-HFC-1234ze | Near azeotrope compositions, mol % E-HFC-1234ze | |
|---|---|---|---|
| | | Minimum | Maximum |
| −20 | 72.7 | 64.2 | 83.0 |
| 60 | 68.4 | 62.4 | 86.0 |
| 100 | 70.6 | 62.4 | 89.4 |

Example 3

Dehydrofluorination of HFC-245fa to HFC-1234ze (E and Z Isomers) Over Carbonaceous Catalyst To a Hastelloy nickel alloy reactor (1.0"OD×0.854" ID×9.5" L)was charged 14.32 g (25 mL) of spherical (8 mesh) three dimensional marix porous carbonaceous material prepared substantially as described in U.S. Pat. No. 4,978,649, incorporated herein by reference. The packed portion of the reactor was heated by a 5"×1" ceramic band heater clamped to the outside of the reactor. A thermocouple, positioned between the reactor wall and the heater measured the reactor temperature. After charging the reactor with the carbonaceous material, nitrogen (10 mLmin) was passed through the reactor and the temperature was raised to 200° C. during a period of one hour and maintained at this temperature for an additional 4 hours. The reactor temperature was then raised to the desired operating temperature and a flow of HFC-245fa and nirogen was started through the reactor.

A portion of the total reactor effluent was sampled on-line for organic product analysis using a gas chromatograph equipped with a mass selective detector (GC-MS). The bulk of the reactor effluent containing organic products and also inorganic acid, such as HF, was treated with aqueous caustic for neutralization.

Results obtained in GC area % are summarized in Table 3.

TABLE 3

| Reactor Temp. (° C.) | HFC-245fa feed (mL/min) | N₂ feed (mL/min) | Mole Percent | | | |
|---|---|---|---|---|---|---|
| | | | E-HFC-1234ze | Z-HFC-1234ze | HFC-245fa | Unknowns |
| 200 | 10 | 20 | 0.1 | ND | 99.6 | 0.3 |
| 250 | 10 | 20 | 0.8 | ND | 99.0 | 0.2 |
| 300 | 10 | 20 | 8.9 | ND | 90.9 | 0.2 |
| 350 | 10 | 10 | 31.6 | 5.7 | 62.3 | 0.4 |
| 350 | 10 | 5 | 42.4 | 8.7 | 48.3 | 0.6 |

ND = not detected

Example 4

Dehydrofluorination of HFC-245fa to HFC-1234ze (E and Z Isomers) Over Fluorided Alumina Catalyst A 15 in×⅜ in Hastelloy tube was filled with 7.96 grams (13 cc) of gamma-alumina ground to 12-20 mesh. The catalyst was activated by heating at 200° C. for 15 minutes under a nitrogen purge (50 sccm, 8.3×10⁻⁷ m³/s). The temperature was raised to 325° C. for 10 minutes, to 400° C. for 20 minutes, and then lowered to 300° C. for 60 minutes. The nitrogen was lowered to 35 sccm (5.8×10⁻⁷ m³/s) and anhydrous HF vapor was fed at 12 sccm (2.0×10⁻⁷ m³/s) for 35 minutes. The temperature was then raised to 325° C. for 60 minutes, to 350° C. for 60 minutes, to 375° C. for 90 minutes, to 400° C. for 30 minutes, and to 425° C. for 40 minutes. The nitrogen was then lowered to 25 sccm ($4.2 \times 10^{-7}$ m$^3$/s) and the HF raised to 20 sccm ($3.3 \times 10^{-7}$ m$^3$/s) for 20 minutes. The nitrogen was then lowered to 15 sccm ($2.5 \times 10^{-7}$ m$^3$/s) and the HF raised to 28 sccm ($4.7 \times 10^{-7}$ m$^3$/s) for 20 minutes. The nitrogen was then lowered to 5 sccm ($8.3 \times 10^{-8}$ m$^3$/s) and the HF raised to 36 sccm ($6.0 \times 10^{-7}$ m$^3$/s) for 20 minutes. The nitrogen was then shut off, and the HF raised to 40 sccm ($6.7 \times 10^{-7}$ m$^3$/s) for 121 minutes.

The temperature of the reactor was set to 375° C., and HFC-245fa was fed at a flow rate of 5.46 mL/hour (20.80 sccm, $3.5 \times 10^{-7}$ m$^3$) and a nitrogen flow rate of 5.2 sccm ($8.7 \times 10^{-8}$ m$^3$). The effluent was analyzed by GC and the results are shown in Table 4.

TABLE 4

| Component | GC Area % |
|---|---|
| E-HFC-1234ze | 71.4 |
| HFC-245fa | 15.2 |
| Z-HFC-1234ze | 12.1 |
| unknown | 1.3 |

Example 5

Azeotropic Distillation for Separation of E-HFC-1234ze From HFC-245fa

A mixture of HF, E-HFC-1234ze, and HFC-245fa is fed to a distillation column for the purpose of purification of the E-HFC-1234ze. The data in Table 5 were obtained by calculation using measured and calculated thermodynamic properties.

TABLE 5

| Component or variable | Column feed | Column overhead (distillate) | Column bottoms |
|---|---|---|---|
| HFC-245fa, mol % | 33.3 | 0 | 62.7 |
| E-HFC-1234ze, mol % | 33.3 | 71.2 | 59 ppm |
| HF, mol % | 33.4 | 28.8 | 37.3 |
| Temp, ° C. | — | −9.1 | 20.5 |
| Pressure, psi (kPa) | — | 24.7 (170) | 26.7 (184) |

Example 6

Azeotropic Distillation for Separation of E-HFC-1234ze from HFC-245fa

A mixture of HF, E-HFC-1234ze, and HFC-245fa is fed to a distillation column for the purpose of purification of the HFC-1234ze. The data in Table 6 were obtained by calculation using measured and calculated thermodynamic properties.

TABLE 6

| Component or variable | Column feed | Column overhead (distillate) | Column bottoms |
|---|---|---|---|
| HFC-245fa, mol % | 22.0 | 0.85 ppm | 100 |
| E-HFC-1234ze, mol % | 56.0 | 71.8 | 3 ppm |
| HF, mol % | 22.0 | 28.2 | — |

TABLE 6-continued

| Component or variable | Column feed | Column overhead (distillate) | Column bottoms |
|---|---|---|---|
| Temp, ° C. | — | −7.7 | 31.1 |
| Pressure, psi (kPa) | — | 24.7 (170) | 26.7 (184) |

Example 7

Azeotropic Distillation for Separation of E-HFC-1234ze from HFC-245fa

A mixture of HF, E-HFC-1234ze, and HFC-245fa is fed to a distillation column for the purpose of purification of the E-HFC-1234ze. The data in Table 7 were obtained by calculation using measured and calculated thermodynamic properties.

TABLE 7

| Component or variable | Column feed | Column overhead (distillate) | Column bottoms |
|---|---|---|---|
| HFC-245fa, mol % | 27.3 | 1 ppm | 100 |
| E-HFC-1234ze, mol % | 63.6 | 87.5 | 4.5 ppm |
| HF, mol % | 9.1 | 12.5 | — |
| Temp, ° C. | — | −7.1 | 31.1 |
| Pressure, psi (kPa) | — | 24.7 (170) | 26.7 (184) |

Example 8

Azeotropic Distillation for Separation of E-HFC-1234ze from HFC-245fa

A mixture of HF, E-HFC-1234ze, and HFC-245fa is fed to a distillation column for the purpose of purification of the HFC-1234ze. The data in Table 8 were obtained by calculation using measured and calculated thermodynamic properties.

TABLE 8

| Component or variable | Column feed | Column overhead (distillate) | Column bottoms |
|---|---|---|---|
| HFC-245fa, mol % | 17.6 | 0.7 ppm | 100 |
| E-HFC-1234ze, mol % | 76.5 | 92.9 | 3 ppm |
| HF, mol % | 5.9 | 7.1 | — |
| Temp, ° C. | — | −6.8 | 31.1 |
| Pressure, psi (kPa) | — | 24.7 (170) | 26.7 (184) |

Example 9

Two Column Azeotropic Distillation for Separation of E-HFC-1234ze from HF

A mixture of HF and E-HFC-1234ze is fed to a distillation set-up comprising 2 columns in series, the first at high pressure (HP) and the second at low pressure (LP). The data in Table 9 were obtained by calculation using measured and calculated thermodynamic properties.

TABLE 9

| Compound or variable | 540 Feed Mixture | 570 Column (510) distillate | 566 E-HFC-1234ze product | 585 Column (520) distillate | 586 HF product |
|---|---|---|---|---|---|
| E-HFC-1234ze, mol % | 71.9 | 69.0 | 100 | 72.0 | — |
| HF, mol % | 28.1 | 31.0 | — | 28.0 | 100 |
| Temp, °C. | — | 68.6 | 90.5 | −18.3 | 36.9 |
| Pres, psi (kPa) | — | 265 (1827) | 267 (1841) | 16.7 (115) | 18.7 (129) |

Example 10

Two Column Azeotropic Distillation for Separation of E-HFC-1234ze from HF

A mixture of HF and E-HFC-1234ze is fed to a distillation set-up comprising 2 columns in series, the first at high pressure (HP) and the second at low pressure (LP). The data in Table 10 were obtained by calculation using measured and calculated thermodynamic properties.

TABLE 10

| Compound or variable | 540 Feed Mixture | 570 Column (510) distillate | 566 E-HFC-1234ze product | 585 Column (520) distillate | 586 HF product |
|---|---|---|---|---|---|
| E-HFC-1234ze, mol % | 76.0 | 69.0 | 100 | 72.0 | — |
| HF, mol % | 24.0 | 31.0 | — | 28.0 | 100 |
| Temp, °C. | — | 68.6 | 76.1 | −18.3 | 26.2 |
| Pres, psi (kPa) | — | 265 (1827) | 267 (1841) | 16.7 (115) | 18.7 (129) |

Example 11

Two Column Azeotropic Distillation for Separation of E-HFC-1234ze from HF

A mixture of HF and E-HFC-1234ze is fed to a distillation set-up comprising 2 columns in series, the first at high pressure (HP) and the second at low pressure (LP). The data in Table 11 were obtained by calculation using measured and calculated thermodynamic properties.

TABLE 11

| Compound or variable | 540 Feed Mixture | 570 Column (510) distillate | 566 E-HFC-1234ze product | 585 Column (520) distillate | 586 HF product |
|---|---|---|---|---|---|
| E-HFC-1234ze, mol % | 79.9 | 69.0 | 100 | 72.0 | — |
| HF, mol % | 20.1 | 31.0 | — | 28.0 | 100 |
| Temp, °C. | — | 68.6 | 76.1 | −18.3 | 26.2 |
| Pres, psi (kPa) | — | 265 (1827) | 267 (1841) | 16.7 (115) | 18.7 (129) |

What is claimed is:

1. An azeotrope or near-azeotrope composition comprising from about 62.4 mole percent to about 89.4 mole percent E-HFC-1234ze and hydrogen fluoride wherein said composition is characterized by a difference between dew point pressure and bubble point pressure that is less than or equal to 3%, based upon bubble point pressure.

2. The azeotrope or near-azeotrope composition of claim 1 wherein said composition comprises from about 62.4 mole percent to about 89.4 mole percent E-HFC-1234ze and from about 37.6 mole percent to about 10.6 mole percent hydrogen fluoride.

3. The azeotrope or near-azeotrope composition of claim 1 wherein said composition comprises from about 62.4 mole percent to about 89.4 mole percent E-HFC-1234ze and from about 37.6 mole percent to about 10.6 mole percent hydrogen fluoride, wherein the vapor pressure is from about 2.8 psi (19 kPa) to about 539 psi (3716 kPa) at a temperature of from about -20° C. to about 100° C.

4. The azeotrope or near-azeotrope composition of claim 1 wherein said composition consists essentially of from about 62.4 mole percent to about 89.4 mole percent E-HFC-1234ze and from about 37.6 mole percent to about 10.6 mole percent hydrogen fluoride, wherein the vapor pressure is from about 2.8 psi (19 kPa) to about 539 psi (3716 KPa) at a temperature of from about -20° C. to about 1000° C.

5. The azeotrope composition of claim 1 wherein said composition comprising from about 68.4 mole percent to about 72.7 mole percent E-HFC-1234ze and from about 31.6 mole percent to about 27.3 mole percent hydrogen fluoride, wherein the vapor pressure is from about 15.5 psi (107 kPa) to about 539 psi (3716 kPa) at a temperature of from about −2° C. to about 100° C.

6. The azeotrope composition of claim 1 wherein said composition consisting essentially of from about 68.4 mole percent to about 72.7 mole percent E-HFC-1234ze and from about 31.6 mole percent to about 27.3 mole percent hydrogen fluoride, wherein the vapor pressure is from about 15.5 psi (107 kPa) to about 539 psi (3716 kPa) at a temperature of from about −20° C. to about 100° C.

7. A process for the separation of E-HFC-1234ze from HFC-245fa comprising:
   a) forming a mixture of E-HFC-1234ze, HFC-245fa, and hydrogen fluoride; and
   b) subjecting said mixture to a distillation step forming a column distillate composition comprising an azeotrope or near-azeotrope composition of hydrogen fluoride and E-HFC-1234ze essentially free of HFC-245fa, wherein said column distillate composition is characterized by a difference between dew point pressure and bubble point pressure that is less than or equal to 3%, based upon bubble point pressure.

8. The process of claim 7 wherein said distillation step further forms a column-bottoms composition comprising HFC-245fa.

9. The process of claim 8 wherein said column-bottoms composition comprises HFC-245fa essentially free of hydrogen fluoride.

10. The process of claim 7 wherein said mixture of E-HFC-1234ze, HFC-245fa, and hydrogen fluoride comprises equimolar quantities of each component.

11. The process of claim 7 wherein said mixture of E-HFC-1234ze, HFC-245fa, and hydrogen fluoride comprises excess E-HFC-1234ze.

12. A process for the separation of E-HFC-1234ze from a mixture comprising an azeotrope or near-azeotrope composition of E-HFC-1234ze and hydrogen fluoride wherein said composition is characterized by a difference between dew point pressure and bubble point pressure that is less than or equal to 3%, based upon bubble point pressure, said process comprising:

a) subjecting said mixture to a first distillation step in which a composition enriched in either (i) hydrogen fluoride or (ii) E-HFC-1234ze is removed as a first distillate composition with a first bottoms composition being enriched in the other of said components (i) or (ii); and b) subjecting said first distillate composition to a second distillation step conducted at a different pressure in which the component enriched as first bottoms composition in (a) is removed in a second distillate composition with a second bottoms composition enriched in the same component which was enriched in the first distillate composition.

13. The process of claim 11 wherein said first bottoms composition or said second bottoms composition comprises E-HFC-1234ze essentially free of hydrogen fluoride.

14. The process of claim 12 wherein said second bottoms composition comprises hydrogen fluoride essentially free of E-HFC-1234ze.

15. The process of claim 12 wherein said first distillation step is carried out at a pressure greater than the pressure of the second distillation step.

16. The process of claim 12 wherein said mixture consists essentially of E-HFC-1234ze in combination with an effective amount of hydrogen fluoride to form an azeotrope or near-azeotrope composition with hydrogen fluoride, said azeotrope or near-azeotrope composition containing from about 62.4 mole percent to about 89.4 mole percent E-HFC-1234ze.

17. A process for the purification of E-HFC-1234ze from a mixture of E-HFC-1234ze, HFC-245fa, and hydrogen fluoride, said process comprising:

a) subjecting said mixture to a first distillation step to form a first distillate comprising an azeotrope or near-azeotrope composition containing E-HFC-1234ze and hydrogen fluoride, wherein said first distillate composition is characterized by a difference between dew point pressure and bubble point pressure that is less than or equal to 3%, based upon bubble point pressure, and a first bottoms comprising HFC-245fa;

b) subjecting said first distillate to a second distillation step from which a composition enriched in either (i) hydrogen fluoride or (ii) E-HFC-1234ze is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed as a third distillate composition with a third bottoms composition enriched in the same component that was enriched in the second distillate composition.

18. A process to produce E-HFC-1234ze comprising:

a) feeding HFC-245fa to a reaction zone for dehydrofluorination to form a reaction product composition comprising E-HFC-1234ze, unreacted HFC-245fa and hydrogen fluoride;

b) subjecting said reaction product composition to a first distillation step to form a first distillate composition comprising an azeotrope or near-azeotrope composition containing E-HFC-1234ze and hydrogen fluoride, wherein said first distillate composition is characterized by a difference between dew point pressure and bubble point pressure that is less than or equal to 3% based upon bubble point pressure, and a first bottoms composition comprising HFC-245fa;

c) subjecting said first distillate composition to a second distillation step from which a composition enriched in either (i) hydrogen fluoride or (ii) E-HFC-1234ze is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (c) is removed as a third distillate composition with a third bottoms composition enriched in the same component that was enriched in the second distillate composition.

19. The process of claim 18, further comprising recycling at least some portion of said first bottoms composition to said reaction zone.

20. The process of claim 18, further comprising recycling at least some portion of said second bottoms composition or said third bottoms composition to said reaction zone.

21. The process of claim 18, further comprising recovering at least some portion of said second bottoms composition or said third bottoms composition as E-HFC-1234ze essentially free of HFC-245fa and hydrogen fluoride.

22. The process of claim 18, further comprising recycling at least some portion of said second bottoms composition or said third bottoms composition to said first distillation step.

* * * * *